(12) United States Patent
Lixin et al.

(10) Patent No.: US 6,177,462 B1
(45) Date of Patent: Jan. 23, 2001

(54) UNSATURATED OXIME ETHERS AND THEIR USE AS FUNGICIDES AND INSECTICIDES

(75) Inventors: Zhang Lixin; Li Zongcheng; Li Zhinian; Zhang Hong; Liu Changling; Li Bin, all of Shenyang (CN); Steven Howard Shaber, Horsham, PA (US)

(73) Assignee: Rohm and Haas Company, Philadelphia, PA (US)

( * ) Notice: Under 35 U.S.C. 154(b), the term of this patent shall be extended for 0 days.

(21) Appl. No.: 09/237,403

(22) Filed: Jan. 26, 1999

Related U.S. Application Data

(60) Provisional application No. 60/106,013, filed on Oct. 28, 1998.

(30) Foreign Application Priority Data

Feb. 10, 1998 (CN) ................................................. 98113756

(51) Int. Cl.$^7$ ...................... C07C 327/00; C07C 233/00; C07C 229/10; A01N 31/327; A01N 43/08
(52) U.S. Cl. .......................... 514/516; 564/163; 564/164; 564/165; 514/516; 514/619; 514/620; 514/523; 514/524; 560/35; 560/9; 560/12; 560/13; 558/252
(58) Field of Search ............................ 564/163, 164–165; 560/35, 9, 12, 13; 558/252; 514/523, 524, 619, 620, 516

(56) References Cited

U.S. PATENT DOCUMENTS

| | | |
|---|---|---|
| 5,055,471 | 10/1991 | de Fraine et al. .................... 514/255 |
| 5,194,662 | * 3/1993 | Brand et al. ............................ 560/35 |
| 5,439,910 | * 8/1995 | De Fraine et al. ................... 514/256 |

FOREIGN PATENT DOCUMENTS

| | | |
|---|---|---|
| 0 370 629 A1 | 5/1990 | (EP) . |
| 0 460 575 A1 | 12/1991 | (EP) . |
| WO 90/07493 | 7/1990 | (WO) . |
| WO 92/13830 | 8/1992 | (WO) . |
| WO 92/18494 | 10/1992 | (WO) . |

* cited by examiner

Primary Examiner—Sabiha N. Qazi
(74) Attorney, Agent, or Firm—Guy T. Donatiello; Thomas D. Rogerson

(57) ABSTRACT

Compounds with fungicidal and insecticidal properties having formula

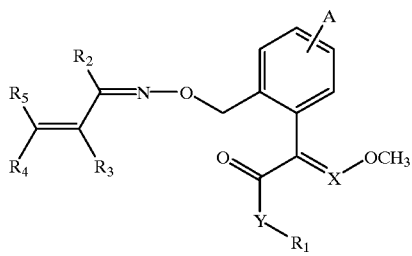

wherein X is N or CH; Y is O, S or $NR_6$;

A is independently hydrogen, halo, cyano, $(C_1-C_{12})$alkyl, or $(C_1-C_{12})$alkoxy;

$R_1$ and $R_6$ is independently hydrogen or $(C_1-C_4)$alkyl;

$R_2$ is independently hydrogen, $(C_1-C_{12})$alkyl, halo $(C_1-C_{12})$alkyl, $(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, or heterocyclic $(C_1-C_4)$alkyl;

$R_3$ is independently hydrogen or $(C_1-C_4)$alkyl;

$R_4$ and $R_5$ is independently hydrogen, $(C_1-C_4)$alkyl, aryl, aralkyl, aryl$(C_2-C_8)$alkenyl, aryl$(C_2-C_8)$alkynyl, heterocyclic, or heterocyclic$(C_1-C_4)$alkyl wherein if one of $R_4$ and $R_5$ is hydrogen or $(C_1-C_4)$alkyl than the other of $R_4$ and $R_5$ is other than hydrogen or $(C_1-C_4)$alkyl, and its enantiomers and stereoisomers and agronomically acceptable salts.

10 Claims, No Drawings

UNSATURATED OXIME ETHERS AND THEIR USE AS FUNGICIDES AND INSECTICIDES

This application claims benefit of provisional application 60/106013, filed Oct. 28, 1998.

The present invention relates to certain oxime ether structures, compositions containing these compounds and methods for controlling fungi and insects by the use of a fungitoxic or insecticidal amount of these compounds.

It is known that compounds having oxime ether structures have been disclosed in US5055471 and are useful as fungicides. However, the effective antimicrobial spectrum of these compounds is still not sufficient. We have discovered new oxime ether structures which possess a substituted alkenyl moiety. These novel compounds possess broad spectrum fungicidal and insecticidal properties.

The novel oxime ethers of the present invention have the Formula (I)

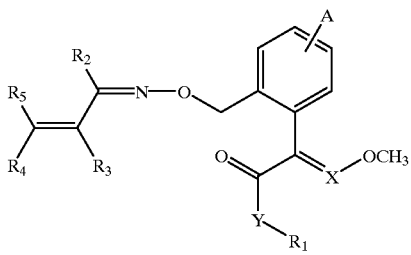

wherein X is N or CH; Y is O, S, or $NR_6$;

A is hydrogen, halo, cyano, $(C_1-C_{12})$alkyl, or $(C_1-C_{12})$alkoxy;

$R_1$ and $R_6$ are independently hydrogen or $(C_1-C_4)$alkyl;

$R_2$ is hydrogen, $(C_1-C_{12})$alkyl, halo$(C_1-C_{12})$alkyl, $(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, or heterocyclic$(C_1-C_4)$alkyl;

$R_3$ is hydrogen or $(C_1-C_4)$alkyl;

$R_4$ and $R_5$ are independently hydrogen, $(C_1-C_4)$alkyl, aryl, aralkyl, aryl$(C_2-C_8)$alkenyl, aryl$(C_2-C_8)$alkynyl, heterocyclic, or heterocyclic$(C_1-C_4)$alkyl wherein only one of $R_4$ and $R_5$ can be selected from the group of hydrogen and $(C_1-C_4)$alkyl.

The aforementioned $(C_1-C_4)$alkyl, $(C_1-C_{12})$alkyl, $(C_2-C_8)$alkenyl, $(C_2-C_8)$alkynyl and $(C_3-C_7)$cycloalkyl groups may be optionally substituted with up to three substituents selected from the group consisting of nitro, halomethyl, $(C_1-C_4)$alkoxycarbonyl, and cyano.

The term alkyl includes both branched and straight chain alkyl groups from 1 to 12 carbon atoms. Typical alkyl groups are methyl, ethyl, n-propyl, isopropyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term alkenyl refers to an ethylenically unsaturated hydrocarbon group, straight or branched, having a chain length of 2 to 8 carbon atoms and 1 or 2 ethylenic bonds. The term haloalkenyl refers to an alkenyl group substituted with 1 to 3 halogen atoms. The term alkynyl refers to an unsaturated hydrocarbon group, straight or branched, having a chain length of 2 to 12 carbon atoms and 1 or 2 acetylenic bonds.

The term aryl includes phenyl or naphthyl, which maybe substituted with up to three substituents independently selected from the group consisting of halogen, cyano, trihalomethyl, phenyl, phenoxy, $(C_1-C_3)$alkyl, $(C_1-C_4)$alkylthio, $(C_1-C_4)$alkylsulfoxide, and halo$(C_1-C_4)$alkyl.

Typical aryl substituents include but are not limited to 2-chlorophenyl, 3-chlorophenyl, 4-chlorophenyl, 2-fluorophenyl, 3-fluorophenyl, 4-fluorophenyl, 4-bromophenyl, 2-methylphenyl, 3-methyphenyl, 4-methylphenyl, 2,4-dibromophenyl, 3,5-difluorophenyl, 2,4,6-trichlorophenyl, 2-chloronaphthyl, 3-(trifluoromethyl) phenyl, 4-(trifluoromethyl)phenyl and 2-iodo-4-methylphenyl.

The term heterocyclic refers to a substituted or unsubstituted six-membered unsaturated ring containing one, two, or three heteroatoms, preferably one, two, or three heteroatoms independently selected from oxygen, nitrogen, and sulfur or to a bicyclic unsaturated ring system containing up to 10 atoms including one heteroatom selected from oxygen, nitrogen, and sulfur. The term heterocyclic also refers to a 5 membered unsaturated ring containing two or three heteroatoms, preferably two heteroatoms independently selected from oxygen, nitrogen or sulfur. Examples of heterocycles include but are not limited to 2-, 3- or 4-pyridinyl, pyrazinyl, 2-, 4-, or 5-pyrimidinyl, pyridazinyl, triazolyl, imidazolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from $(C_1-C_2)$ alkyl, halogen, cyano, nitro and trihalomethyl.

The term aralkyl is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chlorophenyl) ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methyl-phenyl)ethyl, 2-(4-methylphenyl)ethyl, 2-(4-trifluoromethylphenyl)ethyl, 2-(2, 4-dichlorophenyl)-ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichloro-phenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(4-trifluoromethylphenyl)propyl, 3-(2,4-dichlorophenyl)propyl and 3-(3,5-dimethylphenyl)propyl. Typical phenbutyl moities include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methyl-phenyl)butyl and 4-(2,4-dichlorophenyl)butyl.

Halogen or halo is meant to include iodo, fluoro, bromo and chloro moieties.

Because of the C=C or C=N double bonds, the novel compounds of the general Formula I may be obtained in preparation as E/Z isomeric mixtures. These isomers can be separated into individual components by conventional means. The alkenes of Formula I may be obtained in preparation as cis and trans isomeric mixtures which can be separated into individual components by conventional means. Both the individual isomeric compounds and mixtures thereof form subjects of the invention and can be used as fungicides and insecticides.

The present invention also includes the enantiomorphs, agronomically acceptable salts and complexes of Formula (I).

A preferred embodiment of this invention are the compounds, enantiomorphs, salts and complexes of Formula (I') where A is hydrogen, $R_2$ is hydrogen or $(C_1-C_4)$alkyl, $R_3$ and $R_5$ are hydrogen and $R_4$ is aryl, aryl$(C_2-C_8)$alkenyl, and heterocyclic.

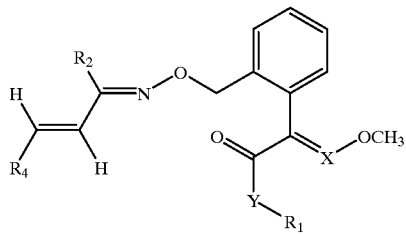

(I')

A more preferred embodiment of this invention are the compounds, enantiomorphs, salts and complexes of Formula (I") where X is CH, Y is O, $R_1$ and $R_2$ are methyl and $R_4$ is aryl.

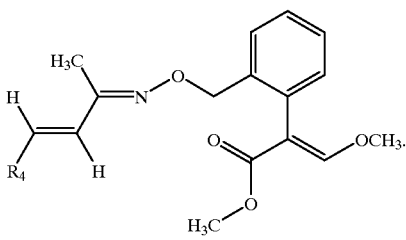

(I")

Typical compounds encompassed by the present invention of Formula I include those compounds presented in Table 1 of Formula IV (X=CH) and Formula V (X=N) where Y is O and A, X, $R_2$, $R_3$, $R_4$, and $R_5$ are defined in Table I Formula IV and V

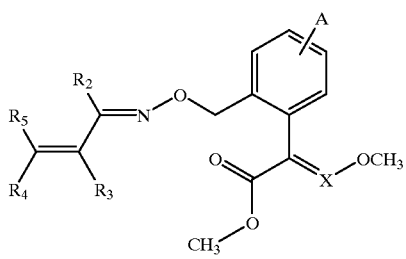

TABLE I

| Compound No. | A | $R_2$ | $R_3$ | $R_5$ | X | $R_4$ | Melting Point/ Property |
|---|---|---|---|---|---|---|---|
| 1.01 | H | $CH_3$ | H | H | CH | 2-Cl—Ph | oil |
| 1.02 | H | $CH_3$ | H | H | CH | 3-Cl—Ph | |
| 1.03a | H | $CH_3$ | H | H | CH | 4-Cl—Ph | oil |
| 1.03b | H | $CH_3$ | H | H | CH | 4-Cl—Ph | oil |
| 1.04 | H | $CH_3$ | H | H | CH | 2-$CF_3$—Ph | |
| 1.05 | H | $CH_3$ | H | H | CH | 3-$CF_3$—Ph | oil |
| 1.06 | H | $CH_3$ | H | H | CH | 4-$CF_3$—Ph | |
| 1.07 | H | $CH_3$ | H | H | CH | 2-$OCH_3$—Ph | oil |
| 1.08 | H | $CH_3$ | H | H | CH | 3-$OCH_3$—Ph | |
| 1.09 | H | $CH_3$ | H | H | CH | 4-$OCH_3$—Ph | |
| 1.10 | H | $CH_3$ | H | H | CH | 2-$CH_3$—Ph | oil |
| 1.11 | H | $CH_3$ | H | H | CH | 3-$CH_3$—Ph | |
| 1.12 | H | $CH_3$ | H | H | CH | 4-$CH_3$—Ph | oil |
| 1.13 | H | $CH_3$ | H | H | CH | 1-Naphthyl | oil |
| 1.14 | H | $CH_3$ | H | H | CH | Ph—CH=CH— | |
| 1.15 | H | $CH_3$ | H | H | CH | 4Cl—PhCH=CH— | oil |
| 1.16 | H | $CH_3$ | H | H | CH | 2-F—Ph | oil |
| 1.17 | H | $CH_3$ | H | H | CH | 3-F—Ph | oil |
| 1.18 | H | $CH_3$ | H | H | CH | 4-F—Ph | oil |
| 1.19 | H | $CH_3$ | H | H | CH | 2-BR—Ph | |
| 1.20 | H | $CH_3$ | H | H | CH | 4-Br—Ph | |
| 1.21 | H | $CH_3$ | H | H | CH | 2-Furfuryl | |
| 1.22 | H | $CH_3$ | H | H | CH | 2,4-Cl—Ph | oil |
| 1.23 | H | $CH_3$ | H | H | CH | 3,4-Cl—Ph | |
| 1.24 | H | $CH_3$ | H | H | CH | 3,5-Cl—Ph | |
| 1.25 | H | $CH_3$ | H | H | CH | 2-Pyridyl | |
| 1.26 | H | $CH_3$ | H | H | CH | 3-Pyridyl | oil |
| 1.27 | H | $CH_3$ | H | H | CH | 4-Pyridyl | |
| 1.28 | H | t-butyl | H | H | CH | 4-Cl—Ph | oil |
| 1.29 | H | t-butyl | H | H | CH | 3-$CF_3$—Ph | |
| 1.30 | H | t-butyl | H | H | CH | 4-$CF_3$—Ph | |
| 1.31 | H | t-butyl | H | H | CH | 4-F—Ph | |
| 1.32 | H | c-$C_3H_5$ | H | H | CH | 4-Cl—Ph | oil |
| 1.33 | H | c-$C_3H_5$ | H | H | CH | 3-$CF_3$—Ph | |
| 1.34 | H | c-$C_3H_5$ | H | H | CH | 4-$CF_3$—Ph | |
| 1.35 | H | c-$C_3H_5$ | H | H | CH | 4-F—Ph | |
| 1.36 | H | 4-Cl—Ph | H | H | CH | 4-Cl—Ph | oil |
| 1.37 | H | 4-Cl—Ph | H | H | CH | 3-$CF_3$—Ph | |
| 1.38 | H | 4-Cl—Ph | H | H | CH | 4-$CF_3$—Ph | |
| 1.39 | H | 4-Cl—Ph | H | H | CH | 4-F—PH | |
| 1.40 | H | $CH_3$ | H | H | N | 2-Cl—Ph | |
| 1.41 | H | $CH_3$ | H | H | N | 3-Cl—Ph | |
| 1.42 | H | $CH_3$ | H | H | N | 4-Cl—Ph | oil |
| 1.43 | H | $CH_3$ | H | H | N | 2-$CF_3$—Ph | |
| 1.44 | H | $CH_3$ | H | H | N | 3-$CF_3$—Ph | |
| 1.45 | H | $CH_3$ | H | H | N | 4-$CF_3$—Ph | |
| 1.46 | H | $CH_3$ | H | H | N | 2-$OCH_3$—Ph | |
| 1.47 | H | $CH_3$ | H | H | N | 2-$CH_3$—Ph | |
| 1.48 | H | $CH_3$ | H | H | N | 3-$CH_3$—Ph | |
| 1.49 | H | $CH_3$ | H | H | N | 4-$CH_3$—Ph | |
| 1.50 | H | $CH_3$ | H | H | N | 1-Naphthyl | |
| 1.51 | H | $CH_3$ | H | H | N | Ph—CH=CH— | |
| 1.52 | H | $CH_3$ | H | H | N | 2-F—Ph | |
| 1.53 | H | $CH_3$ | H | H | N | 3-F—Ph | |
| 1.54a | H | $CH_3$ | H | H | N | 4-F—Ph | oil |
| 1.54b | H | $CH_3$ | H | H | N | 4-F—Ph | oil |
| 1.55 | H | $CH_3$ | H | H | N | 2-Br—Ph | |
| 1.56 | H | $CH_3$ | H | H | N | 4-Br—Ph | |
| 1.57 | H | $CH_3$ | H | H | N | 2-Furfuryl | |
| 1.58 | H | $CH_3$ | H | H | N | 3,5-Cl—Ph | |
| 1.59 | H | $CH_3$ | H | H | N | 2-Pyridyl | |
| 1.60 | H | $CH_3$ | H | H | N | 3-Pyridyl | |
| 1.61 | H | $CH_3$ | H | H | N | 4-Pyridyl | |
| 1.62 | H | t-butyl | H | H | N | 4-Cl—Ph | |
| 1.63 | H | t-butyl | H | H | N | 3-$CF_3$—Ph | |
| 1.64 | H | t-butyl | H | H | N | 4-$CF_3$—Ph | |
| 1.65 | H | t-butyl | H | H | N | 4-F—Ph | |
| 1.66 | H | c $C_3H_5$ | H | H | N | 4-Cl—Ph | |
| 1.67 | H | c-$C_3H_5$ | H | H | N | 3-$CF_3$—Ph | |
| 1.68 | H | c-$C_3H_5$ | H | H | N | 4-$CF_3$—P | |
| 1.69 | H | c-$C_3H_5$ | H | H | N | 4-F—Ph | |
| 1.70 | H | 4-Cl—Ph | H | H | N | 4-Cl—Ph | |

TABLE I-continued

| Compound No. | A | $R_2$ | $R_3$ | $R_5$ | X | $R_4$ | Melting Point/ Property |
|---|---|---|---|---|---|---|---|
| 1.71 | H | 4-Cl—Ph | H | H | N | 3-$CF_3$—Ph | |
| 1.72 | H | 4-Cl—Ph | H | H | N | 4-$CF_3$—Ph | |

Note that 1.03a and 1.03b are separated oxime isomers.

Typical compounds encompassed by the present invention of Formula I include those compounds presented in Table II of Formula VII (X is NH) and A, X, $R_2$, $R_3$, $R_4$, and $R_5$ are defined in Table II Formula VII

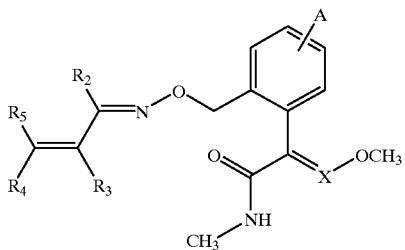

TABLE II

| Compound No. | A | $R_2$ | $R_3$ | $R_5$ | X | $R_4$ | Melting Point/ Property |
|---|---|---|---|---|---|---|---|
| 2.01 | H | $CH_3$ | H | H | N | 2-Cl—Ph | |
| 2.02 | H | $CH_3$ | H | H | N | 3-Cl—Ph | |
| 2.03 | H | $CH_3$ | H | H | N | 4-Cl—Ph | oil |
| 2.04 | H | $CH_3$ | H | H | N | 2-$CF_3$—Ph | |
| 2.05 | H | $CH_3$ | H | H | N | 3-$CF_3$—Ph | |
| 2.06 | H | $CH_3$ | H | H | N | 4-$CF_3$—Ph | |
| 2.07 | H | $CH_3$ | H | H | N | 2-$OCH_3$—Ph | |
| 2.08 | H | $CH_3$ | H | H | N | 2-$CH_3$—Ph | |
| 2.09 | H | $CH_3$ | H | H | N | 3-$CH_3$—Ph | |
| 2.10 | H | $CH_3$ | H | H | N | 4-$CH_3$—Ph | |
| 2.11 | H | $CH_3$ | H | H | N | 1-Naphthyl | |
| 2.12 | H | $CH_3$ | H | H | N | Ph—CH=CH— | |
| 2.13 | H | $CH_3$ | H | H | N | 2-F—Ph | |
| 2.14 | H | $CH_3$ | H | H | N | 3-F—Ph | |
| 2.15 | H | $CH_3$ | H | H | N | 4-F—Ph | |
| 2.16 | H | $CH_3$ | H | H | N | 4-F—Ph | |
| 2.17 | H | $CH_3$ | H | H | N | 2-Br—Ph | |
| 2.18 | H | $CH_3$ | H | H | N | 4-Br—Ph | |
| 2.19 | H | $CH_3$ | H | H | N | 2-Furfuryl | |
| 2.20 | H | $CH_3$ | H | H | N | 3-Pyridyl | |
| 2.21 | H | $CH_3$ | H | H | N | 4-Pyridyl | |
| 2.22 | H | t-butyl | H | H | N | 4-Cl—Ph | |
| 2.23 | H | t-butyl | H | H | N | 3-$CF_3$—Ph | |
| 2.24 | H | t-butyl | H | H | N | 4-$CF_3$—Ph | |
| 2.25 | H | t-butyl | H | H | N | 4-F—Ph | |
| 2.26 | H | c-$C_3H_5$ | H | H | N | 4-Cl—Ph | |
| 2.27 | H | c-$C_3H_5$ | H | H | N | 3-$CF_3$—Ph | |
| 2.28 | H | c-$C_3H_5$ | H | H | N | 4-$CF_3$—Ph | |
| 2.29 | H | c-$C_3H_5$ | H | H | N | 4-F—Ph | |
| 2.30 | H | 4-Cl—Ph | H | H | N | 4-Cl—Ph | |
| 2.31 | H | 4-Cl—Ph | H | H | N | 3-$CF_3$—Ph | |

1.03a, 1.03b and 1.54a, 1,54b are separated oxime isomers. As used herein, "Ph" is understood to be phenyl, and "c-" indicates a cyclic compound.

Scheme A describes the preparation of compounds of the Formula (I). where X is CH or N, and Y is O (compounds of formula IV and V). The unsaturated oximes (III) are reacted with the appropriately substituted benzyl derivatives (II) where Z is a halogen, such as bromo, chloro or iodo, preferably a benzyl bromide. An unsaturated oxime represented by the general formula (III) is treated, at room temperature, with an appropriate base to form an anion, followed by the addition of the benzyl bromides (II). Typical bases employed are metal hydrides such as sodium hydride, alkoxides such as sodium methoxide and hydroxide bases such as sodium or potassium hydroxide and alkali bases such as sodium or potassium carbonate. Typical solvents employed with hydride bases are N,N-dimethyl-formamide (DMF) and tetrahydrofuran (THF); with hydroxide bases, solvents such as DMF, THF, methyl ethyl ketone (MEK) and acetone; and with alkali bases, solvents such as DMF, acetone, and MEK.

As shown in Scheme A, the oxime appears in the E position (assuming $R_3C=CR_4R_5$ is the larger substituent). It should be recognized that the Z isomer can also be produced as well as mixtures. When isomers are produced they are designated isomer A (higher $R_f$ on thin layer chromatography) and isomer B (lower $R_f$ on thin layer chromatography). The determination of which isomer, A or B possesses the E or Z geometry can be made by such conventional techniques as X ray crystallography or by spectroscopic means such as nuclear magnetic resonance spectroscopy.

Scheme A

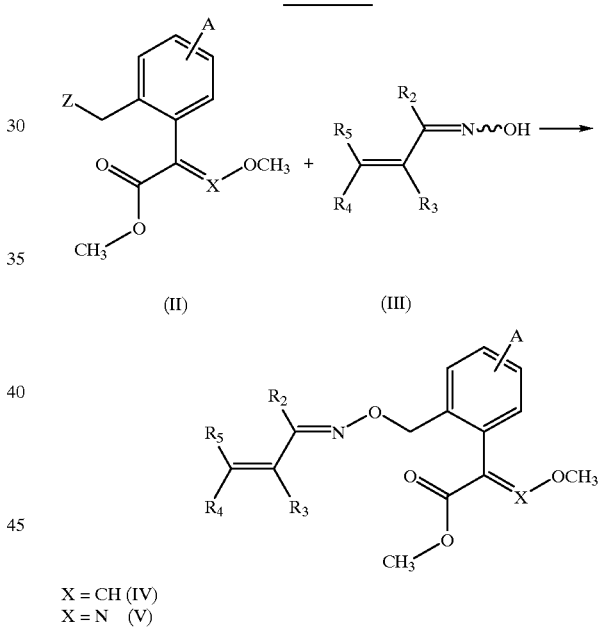

X = CH (IV)
X = N  (V)

Compounds of formula IV (X is CH) are prepared by alkylation with methyl E-α-(2-bromomethylphenyl)-β-methoxyacrylate in the presence of a base, preferably NaOH or KOH, in a solvent, preferably acetone or methyl ethyl ketone. Methyl E-α-(2-bromomethylphenyl)-β-methoxyacrylate, as a single E isomer, can be prepared in two steps from 2-methylphenylacetate as described previously in U.S. Pat. No. 4,914,128, columns 3–4. Compounds of formula V (X=N) are prepared by the reaction with methyl E-2-(bromomethyl)phenylglyoxylate O-methyloxime in the presence of a base, preferably NaOH or KOH, in a solvent, preferably acetone or methyl ethyl ketone. Methyl 2-(bromomethyl)phenylglyoxylate O-methyloxime can be prepared as described in U.S. Pat. No. 4,999,042, columns 17–18 and 5,157,144, columns 17–18. Methyl 2-(bromomethyl)phenylglyoxylate O-methyl-oxime is prepared from methyl 2-methylphenylacetate by treatment with an alkyl nitrite under basic conditions to provide after methylation, methyl 2-methyl-phenyl-glyoxalate O-methyl oxime which can also be prepared from methyl 2-methyl-phenylglyoxalate by treatment with 2-hydroxylamine hydrochloride and methylation or by treatment with methoxylamine hydrochloride.

4th Ed, pp. 906–907 and references therein. The oximes of the general formula (III) when obtained as a mixture of syn or anti oxime isomers can be separated into individual isomers and alkylated as described in scheme A and B. When a mixture of oximes of the general formula (III) are used in Scheme A and B the compounds of the formula IV, V and VII can be separated into their individual isomers by conventional chromatographic techniques.

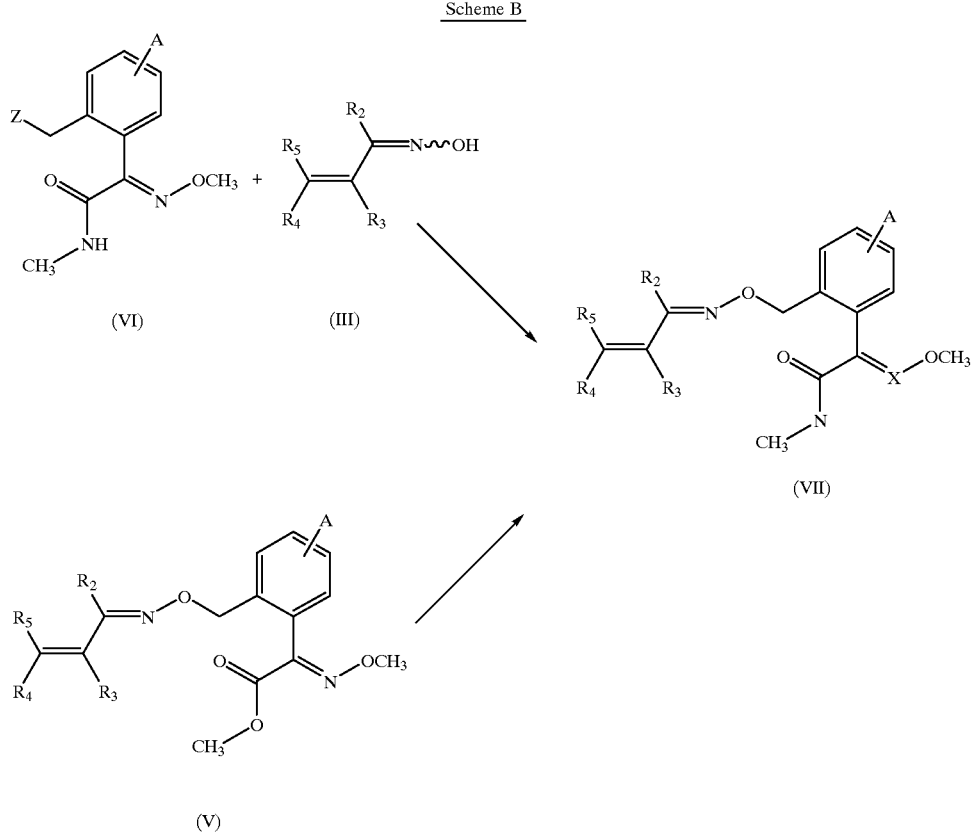

As shown in scheme B compounds of formula VII (X is N) can be prepared by the aminolysis of oximinoacetate (V). The aminolysis of oximinoacetate to oximinoacetamides has been described in U.S. Pat. No. 5,185,342, cols. 22, 48 and 57, 5,221,691, cols. 26–27 and 5,407,902, col. 8. For example, compounds of Table I of formula V where X is N and Y is O are treated with 40% aqueous methylamine in methanol to provide compounds of Table II of formula VIII where Y is NH. Alternatively, as is shown in scheme B intermediate unsaturated oximes (III) are reacted with N-Methyl (E)-2-methoxyimino-2-[2-(bromomethyl) phenyl]-acetamide in the presence of a base such as an hydroxide base preferably in a solvent such as acetone or methyl ethyl ketone to provide compounds of Table II of formula (VII). N-Methyl (E)-2-methoxy-imino-2-[2-(bromomethyl)phenyl]-acetamide is described in U.S. Pat. No. 5,387,714, col. 13.

The oximes of the general formula (III) can be obtained, as shown in scheme C, by reacting the corresponding α,β-unsaturated aldehyde or ketone (VIII) with hydroxylamine hydrochloride from room temperature to reflux, preferably at room temperature, in an appropriate solvent such as methanol or ethanol in the presence of an appropriate alkali such as sodium hydroxide or potassium carbonate. A general description of the synthesis of oximes with hydroxyl amine is described in March, *Advanced Organic Chemistry*,

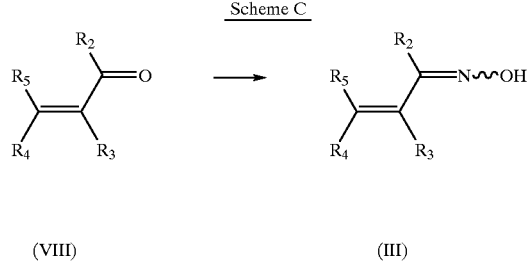

The α,β-unsaturated aldehydes or ketones (VIII) can be prepared by conventional condensation techniques. A extensive description of the synthesis of α,β-unsaturated aldehydes or ketones (enones) is described in March, *Advanced Organic Chemistry*, 4th Ed, pp. 937–955 and references therein. For example *Organic Reactions*, Volume 16 describes the general aldol condensation of ketones and aldehydes. For compounds of formula I of this invention, in general the ketones or aldehydes can be $R_4COR_5$ where $R_4$ and $R_5$ are defined previously or the ketones and aldehydes can be $R_2COCH_2R_3$ where $R_2$ and $R_3$ are defined as in formula I. Typically the ketone is dissolved in a hydroxylic solvent, such as methanol or ethanol, to which is added dropwise a solution of the aldehyde in an aqueous basic solution. The typical bases used can be alkali metal hydroxides, such as barium, potassium or sodium hydroxide and the dropwise addition is conducted from 0° C. to 35° C. preferably at ambient temperature. When the enone is derived from acetone ($R_2$ is methyl and $R_3$ is hydrogen) the solvent is preferably acetone to which is added $R_4COR_5$ followed by the aqueous hydroxide solution.

The following examples are illustrative of the present invention

EXAMPLE 1

Methyl 3-methoxy-2-[2-((((1-methyl-3-(2'-chlorophenyl)-2-propenylidene)amino)oxy)-methyl)phenyl]propenoate (Compound 1.01, Table 1).

In a 250 ml single neck flask was charged 14 g (99.6 mmoles, 1.0 eq) of o-chlorobenzaldehyde dissolved in 30 ml of acetone. To this was added 5 g of a 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 13.8 g of (E)-4-(2-chlorophenyl)-3-buten-2-one as a faintly yellow oil in 76.9% yield.

In a 250 ml single neck flask was charged 5.4 g (29.9 mmoles, 1.0 eq.) of (E)-4-(2-chlorophenyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.4 g of 4-(2-chlorophenyl)-3-buten-2-one 2-oxime (E/Z mixture of oximes) as an oil in 58.1% yield.

In a 250 ml single neck flask was charged a suspension of 60% sodium hydride 0.2 g (5.0 mmoles, 1.03 eq., washed with n-hexane) in 10 ml of N,N-dimethylformamide (DMF). To this agitated suspension, stirring at room temperature, was added dropwise 0.95 g of 4-(2-chlorophenyl)-3-buten-2-one 2-oxime (4.86 mmoles, 1.0 eq) in 10 ml of N,N-dimethylformamide After 30 minutes, 1.43 g (5.01 mmoles, 1.0 eq) of methyl (E)-α-[2-(bromomethyl)phenyl]-β-methoxyacrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.45 g of methyl 3-methoxy-2-[2-((((1-methyl-3-(2'-chlorophenyl)2-propenylidene) amino)-oxy)methyl)phenyl]propenoate (single oxime isomer) as a faint yellow oily substance in 23.1% yield. $^1$HNMR (90 MHz, CDCl3): 2.07 (3 H, s), 3.68 (3 H, s), 3.80 (3 H, s),5.10 (2 H, s), 6.6–6.8 (2 H, d), 7.0–7.6 (8 H, m), and7.57 (1 H, s).

EXAMPLE 2a

Methyl 3-methoxy-2-[2-((((1-methyl-3-(4'-chlorophenyl)-2-propenylidene)amino)oxy)-methyl)phenyl]propenoate (Compound 1.03a, Table 1).

In a 250 ml single neck flask was charged 14 g (99.6 mmoles, 1.0 eq) of p-chlorobenzaldehyde dissolved in 30 ml of acetone. To this was added 5 g of 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 15.5 g of (E)-4-(4-chlorophenyl)-3-buten-2-one as a faintly yellow oil in 86.2% yield.

In a 250 ml single neck flask was charged 5.4 g (29.9 mmoles, 1.0 eq.) of (E)-4-(2-chlorophenyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.2 g of 4-(4-chlorophenyl)-3-buten-2-one 2-oxime (E/Z mixture of oxime isomers) as an oil in 54.7% yield.

In a 250 ml single neck flask was charged a suspension of 60% sodium hydride 0.2 g (5.0 mmoles, 1.03 eq., washed with n-hexane) in 10 ml of N,N-dimethylformamide (DMF). To this agitated suspension, stirring at room temperature, was added dropwise 0.95 g of 4-(4-chlorophenyl)-3-buten-2-one 2-oxime (4.86 mmoles, 1.0 eq) in 10 ml of N,N-dimethylformamide After 30 minutes, 1.43 g (5.01 mmoles, 1.0 eq) of methyl (E)-α-[2-(bromomethyl)phenyl]-β-methoxyacrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.55 g of methyl 3-methoxy-2-[2-((((1-methyl-3-(4'-chlorophenyl)-2-propenylidene) amino) oxy)methyl)phenyl]propenoate (single oxime isomer 1.03a) as a faint yellow oily substance in 27.5% yield. $^1$HNMR (90 MHz, CDCl3): 2.07 (3 H, s), 3.68 (3 H, s), 3.80 (3 H, s), 5.10 (2 H, s), 6.78(2 H, s), 7.0–7.4 (8 H, m), and 7.57 (1 H, s).

Separation of E/Z mixture of oxime isomers of 4-(4-chlorophenyl)-3-buten-2-one 2-oxime A 3:2 mixture of oxime isomers of 4-(4-chlorophenyl)-3-buten-2-one 2-oxime was chromatographed in two batches using silica gel flash chromatography: 1.4 g of the oxime mixture using 1:4 EtOAC/hexane and 3 g of the oxime mixture with 1:3 EtOAc/hexane. the The two separations were combined to give 1.14 g isomer of the higher $R_f$ material ($R_f$=0.36 in 1:3 EtOAc:Hexanes), designated as oxime isomer A, as a white/yellow solid and 1.04 g isomer of a lower $R_f$ material ($R_f$=0.21 in 1:3 EtOAc:Hexanes), designated as oxime isomer B product as an off-white solid. Alkylation of oxime isomer A provided material identical with that prepared in Example 2a as compound 1.03a.

EXAMPLE 2b

Methyl 3-methoxy-2-[2-(((( 1-methyl-3-(4'-chlorophenyl)-2-propenylidene)amino)oxy)-methyl)phenyl]propenoate (Compound 1.03b, Table 1).

To a 1oz vial was charged 0.94 g (1.0 eq., 4.8 mmole) of 4-(4-chlorophenyl)-3-buten-2-one 2-oxime isomer B (lower $R_f$ oxime isomer) neat, 1.37 g (1.0 eq., 4.8 mmole) of methyl (E)-α-[2-(bromomethyl)phenyl]-β-methoxyacrylate in 6 ml DMF, and 0.40 g (1.5 eq., 7.2 mmole) KOH powdered pellets neat. The reaction was stirred at room temperature for 4 hrs. with monitoring by TLC after which the reaction was quenched with ethyl acetate and water, separation of the phases, drying and removal of the solvent gave 2.2 g of the crude product as a yellow oil. The crude product was purified by flash chromatograhy silica gel with 1:3 EtOAc/hexane eluant to give 500 mg of methyl 3-methoxy-2-[2-((((1-methyl-3-(4'-chlorophenyl)-2-propenylidene) amino)oxy)methyl)phenyl]propenoate (single oxime isomer 1.03b) as a light yellow oil in 26.0% yield.

NMR (H1, 300 MHz): 2.08(s,3 H), 3.63(s,3 H), 3.78(s,3 H), 5.07(s,2 H), 6.8–6.85(d,1 H), 7.1–7.6(m,10 H)

EXAMPLE 3

Methyl 3-methoxy-2-[2-((((1-methyl-3-(3'-trifluoromethylphenyl)-2-propenylidene)amino)-oxy)methyl)phenyl]propenoate (Compound 1.05 Table 1).

In a 250 ml single neck flask was charged 7.5 g (43.1 mmoles,1.0 eq) of m-trifluoromethylbenzaldehyde dissolved in 15 ml of acetone. To this was added 17.2 g of 10% aqueous sodium hydroxide solution (43 mmoles, 1.0 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 9.5 g of 4-(3-trifluoromethylphenyl)-3-buten-2-one as a faintly yellow oil in 88.7% yield.

In a 250 ml single neck flask was charged 6.4 g (29.9 mmoles, 1.0 eq.) of 4-(3-trifluoromethylphenyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50ml), and then extracted with ethyl acetate (2×50 ml). The organic phase was dried and concentrated, to obtain 4.4 g of 4-(3-trifluoromethylphenyl)-3-buten-2-one 2-oxime (E/Z mixture of isomers) as an oil in 64.2% yield.

In a 250 ml single neck flask was charged a suspension of 60% sodium hydride 0.2 g (5.0 mmoles, 1.0 eq., washed with n-hexane) in 10 ml of N,N-dimethylformamide (DMF). To this agitated suspension, stirring at room temperature, was added dropwise 1.15 g of 4-(3-trifluoromethylphenyl)-3-buten-2-one 2-oxime (5.02 mmoles, 1.0 eq) in 10 ml of N,N-dimethylformamide After 30 minutes, 1.43 g (5.01 mmoles, 1.0 eq) of methyl (E)-α-[2-(bromomethyl)phenyl]-β-methoxyacrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.55 g of methyl 3-methoxy-2-[2-((((1-methyl-3-(3'-trifluoromethylphenyl)-2-propenylidene)amino)oxy)methylphenyl]propenoate (a single oxime isomer)as a faint yellow oily substance in 29.9% yield.

$^1$HNMR (90 MHz, CDCl3): 2.08 (3 H, s), 3.68 (3 H, s), 3.79 (3 H, s), 5.12 (2 H, s), 6.7–6.9(2 H, m), 7.0–7.8 (8 H, m), and 7.59 (1 H, s).

IR absorption peaks: 1697 cm$^{-1}$, 1620 cm$^{-1}$, 1258 cm$^{-1}$, 1110 cm$^{-1}$

EXAMPLE 4

Methyl 3-methoxy-2-[2-((((1-methyl-3-(2'methoxyphenyl)-2-propenylidene)amino)-oxy)-methyl)phenyl] propenoate (Compound 1.07 Table 1).

In a 250 ml single neck flask was charged 13.6 g (100 mmoles,1.0 eq) of o-methoxybenzaldehyde dissolved in 30 ml of acetone. To this was added 5 g of 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 14.5 g of 4-(2-methoxyphenyl)-3-buten-2-one as a faintly yellow oil in 82.3% yield.

In a 250 ml single neck flask was charged 5.28 g (.30.0 mmoles, 1.0 eq.) of 4-(2-methoxyphenyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.1 g of 4-(2-methoxyphenyl)-3-buten-2-one 2-oxime (E/Z mixture of isomers) as an oil in 54.1% yield.

In a 250 ml single neck flask was charged a suspension of 60% sodium hydride 0.2 g (5.0 mmoles, 1.0 eq., washed with n-hexane) in 10 ml of N,N-dimethylformamide (DMF). To this agitated suspension, stirring at room temperature, was added dropwise 0.95 g of 4-(2-methoxyphenyl)-3-buten-2-one 2-oxime (4.97 mmoles, 1.0 eq) in 10 ml of N,N-dimethylformamide After 30 minutes, 1.43 g (5.01 mmoles, 1.01 eq) of methyl (E)-α-[2-(bromomethyl) phenyl]-β-methoxyacrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.45 g of methyl 3-methoxy-2-[2-((((1-methyl-3-(3'-trifluoromethylphenyl)-2-propenylidene)amino)oxy)methylphenyl] propenoate (enriched in one major oxime isomer) as a faint yellow oily substance in 22.7% yield.

$^1$HNMR (90 MHz, CDCl3): 2.11 (3 H, s), 3.68 (3 H, s), 3.82 (3 H, s), 3.87 (3 H,s) 5.10 (2 H, s), 6.8–7.0 (2 H, m), 7.1–7.8 (8 H,m) and7.58 (1 H, s).

EXAMPLE 5

Methyl 3-methoxy-2-[2-((((1-methyl-3-(2'methylphenyl)-2-propenylidene)amino)oxy)-methyl)phenyl]propenoate (Compound 1.10 Table 1).

In a 250 ml single neck flask was charged 12.0 g (100 mmoles,1.0 eq) of o-tolualdehyde dissolved in 30 ml of acetone. To this was added 5 g of 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 13.8 g of 4-(o-tolyl)-3-buten-2-one as a faintly yellow oil in 86.3% yield.

In a 250 ml single neck flask was charged 4.8 g (30.0 mmoles, 1.0 eq.) of 4-(2-methoxyphenyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.0 g of 4-(o-toylyl)-3-buten-2-one 2-oxime (E/Z mixture of isomers) as an oil in 57.1 % yield.

In a 250 ml single neck flask was charged a suspension of 60% sodium hydride 0.2 g (5.0 mmoles, 1.0 eq., washed with n-hexane) in 10 ml of N,N-dimethylformamide (DMF). To this agitated suspension, stirring at room temperature, was added dropwise 0.88 g of 4-(o-tolyl)-3-buten-2-one 2-oxime (5.03 mmoles, 1.0 eq) in 10 ml of N,N-dimethylformamide After 30 minutes, 1.43 g (5.01 mmoles, 1.01 eq) of methyl (E)-α-[2-(bromomethyl)phenyl]-β-methoxyacrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.45 g of methyl 3-methoxy-2-[2-((((1-methyl-3-(o-tolyl)-2-propenylidene)amino)oxy)-methylphenyl]propenoate (one major oxime isomer) as a faint yellow oily substance in 23.7% yield.
$^1$HNMR (90 MHz, CDCl3): 2.05 (3 H, s), 2.33 (3 H, s), 3.62 (3 H, s), 3.74 (3 H,s), 5.03 (2 H, s), 6.8–7.0 (2 H, m), 7.0–7.5 (8 H, m) and 7.37 (1 H, s).

EXAMPLE 6

Methyl 3-methoxy-2-[2-((((1-methyl-3-(4'methylphenyl)-2-propenylidene)amino)oxy)-methyl)phenyl]propenoate (Compound 1.12 Table 1).

In a 250 ml single neck flask was charged 12.1 g (100 mmoles,1.0 eq) of p-tolualdehyde dissolved in 30 ml of acetone. To this was added 5 g of 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 13.5 g of 4-(p-tolyl)-3-buten-2-one as a faintly yellow oil in 84.3% yield.

In a 250 ml single neck flask was charged 4.8 g (30.0 mmoles, 1.0 eq.) of 4-(p-tolyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.2 g of 4-(p-tolyl)-3-buten-2-one 2-oxime (E/Z mixture of isomers) as an oil in 60.9% yield.

In a 250 ml single neck flask was charged a suspension of 60% sodium hydride 0.2 g (5.0 mmoles, 1.0 eq., washed with n-hexane) in 10 ml of N,N-dimethylformamide (DMF). To this agitated suspension, stirring at room temperature, was added dropwise 0.88 g of 4-(p-tolyl)-3-buten-2-one 2-oxime (5.02 mmoles, 1.0 eq) in 10 ml of N,N-dimethylformamide After 30 minutes, 1.43 g (5.01 mmoles, 1.0 eq) of methyl (E)-α-[2-(bromomethyl)phenyl]-β-methoxyacrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.44 g of methyl 3-methoxy-2-[2-((((1-methyl-3-(p-tolyl)-2-propenylidene)amino)- oxy) methylphenyl]propenoate (one major oxime isomer) as a faint yellow oily substance in 23.7% yield.
$^1$HNMR (90 MHz, CDCl3):2.04 (3 H, s), 2.31 (3 H, s), 3.64 (3 H,s), 3.76 (3 H, s), 5.04 (2 H, s), 6.73 (2 H,s), 7.0–7.5 (8 H, m) and 7.48 (1 H, s).

EXAMPLE 7

Methyl 3-methoxy-2-[2-((((1-methyl-3-(1-naphthyl)-2-propenylidene)amino)oxy)-methyl)phenyl]propenoate (Compound 1.13 Table 1).

In a 250 ml single neck flask was charged 15.6 g (100 mmoles,1.0 eq) of 1-naphthaldehyde dissolved in 30 ml of acetone. To this was added 5 g of 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 16.5 g of 4-(1-naphthyl)-3-buten-2-one as a faintly yellow oil in 84.3% yield.

In a 250 ml single neck flask was charged 5.88 g (30.3 mmoles, 1.0 eq.) of 4-(1-naphthyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.9 g of 4-(1-naphthyl)-3-buten-2-one 2-oxime (E/Z mixture of isomers) as an oil in 62% yield.

In a 250 ml single neck flask was charged a suspension of 60% sodium hydride 0.2 g (5.0 mmoles, 1.0 eq., washed with n-hexane) in 10 ml of N,N-dimethylformamide (DMF). To this agitated suspension, stirring at room temperature, was added dropwise 1.05 g of 4-(1-naphthyl)-3-buten-2-one 2-oxime (5.02 mmoles, 1.0 eq) in 10 ml of N,N-dimethylformamide After 30 minutes, 1.43 g (5.01 mmoles, 1.00 eq) of methyl (E)-α-[2-(bromomethyl)phenyl]-β-methoxyacrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.75 g of methyl 3-methoxy-2-[2-((((1-methyl-3-(1-naphthyl)-2-propenylidene)amino) oxy)methylphenyl]propenoate (one major oxime isomer) as a faint yellow oily substance in 36.1% yield.
$^1$HNMR (90 MHz, CDCl3)"2.02 (3 H, s), 3.69 (3 H, s), 3.80 (3 H, s), 5.14 (2 H,s), 6.8–7.0 (2 H, d), 7.1–8.2 (11 H, m) and 7.58 (1 H, s).

EXAMPLE 8

Methyl 3-methoxy-2-[2-((((1-methyl-3-(2-phenylethenyl)-2-propenylidene)amino)-oxy)methyl)phenyl]propenoate (Compound 1.14 Table 1).

In a 250 ml single neck flask was charged 13.2 g (100 mmoles,1.0 eq) of cinnamaldehyde dissolved in 30 ml of acetone. To this was added 5 g of 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 15.7 g of 4-(2-phenylethenyl)-3-buten-2-one as a faintly yellow oil in 91% yield.

In a 250 ml single neck flask was charged 5.28 g (30 mmoles, 1.0 eq.) of 4-(1-naphthyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.4 of 4-(2-phenylethenyl)-3-buten-2one 2-oxime (E/Z mixture of isomers) as an oil in 60.6% yield.

In a 250 ml single neck flask was charged a suspension of 60% sodium hydride 0.2 g (5.0 mmoles, 1.0 eq., washed with n-hexane) in 10 ml of N,N-dimethylformamide (DMF). To this agitated suspension, stirring at room temperature, was added dropwise 0.94 g of 4-(2-phenylethenyl)-3-buten-2-one 2-oxime (5.02 mmoles, 1.0 eq) in 10 ml of N,N-dimethylformamide After 30 minutes, 1.43 g (5.01 mmoles, 1.0 eq) of methyl (E)-α-[2-(bromomethyl)phenyl]-β-methoxy-acrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.65 g of methyl 3-methoxy-2-[2-((((1-methyl-3-(2-phenylethenyl)-2-propenylidene) amino)-oxy)methylphenyl]propenoate (one major oxime isomer) as a faint yellow oily substance in 33.2% yield.
$^1$HNMR (90 MHz, CDCl3):2.01 (3H, s), 3.62 (3 H, s), 3.75 (3 H, s), 5.02 (2 H, s(, 6.1–6.8 (4 H, m), 7.0–7.5 (9 H, m) and 7.47 (1 H, s)

EXAMPLE 9
Methyl 3-methoxy-2-[2-((((1-methyl-3-(4-fluorophenyl)-2-propenylidene)amino)oxy)-methyl)phenyl]propenoate (Compound 1.18 Table 1).

In a 250 ml single neck flask was charged 12.4 g (100 mmoles,1.0 eq) of 4-fluorobenzaldehyde dissolved in 30 ml of acetone. To this was added 5 g of 10% aqueous sodium hydroxide solution (12.5 mmoles, 0.125 eq), dropwise and during the course of addition, temperature was kept no higher than 25° C., while the mixture was agitated continuously for 30 minutes. To the mixture was added 50 ml of water, followed by 100 ml of ethyl acetate, the phases were separated and the organic phase was washed with water three times and then dried, and concentrated to obtain 13.5 g of 4-(4-fluorophenyl)-3-buten-2-one as a faintly yellow oil in 82.3% yield.

In a 250 ml single neck flask was charged 4.92 g (30 mmoles, 1.0 eq.) of 4-(4-fluorophenyl)-3-buten-2-one and 5.2 g (75.4 mmoles, 2.5 eq) of hydroxylamine hydrochloride and 6 g of 50% sodium hydroxide (75 mmoles, 2.5 eq) and 100 ml of methanol. The reaction mixture was stirred at reflux for 2 hours. The reaction mixture was concentrated, diluted with water (50 ml), and then extracted with ethyl acetate (2×50 ml). The organic phase was dried and concentrated, to obtain 3.4 of 4-(4-fluorophenyl)-3-buten-2one 2-oxime (E/Z mixture of isomers) as an oil in 63.3% yield.

In a 250 ml single neck flask was charged a suspension of 60% sodium hydride 0.2 g (5.0 mmoles, 1.0 eq., washed with n-hexane) in 10 ml of N,N-dimethylformamide (DMF). To this agitated suspension, stirring at room temperature, was added dropwise 0.90 g of 4-(4-fluorophenyl)-3-buten-2-one 2-oxime (5.02 mmoles, 1.0 eq) in 10 ml of N,N-dimethylformamide After 30 minutes, 1.43 g (5.01 mmoles, 1.0 eq) of methyl (E)-α-[2-(bromomethyl)phenyl]-β-methoxy-acrylate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.55 g of methyl 3-methoxy-2-[2-((((1-methyl-3-(4-fluorophenyl)-2-propenylidene) amino)-oxy)methylphenyl]propenoate (one major oxime isomer) as a faint yellow oily substance in 28.6% yield.
$^1$HNMR ( 90 MHz, CDCl3): 2.07 (3 H, s), 3.68 (3 H, s), 3.80 (3 H, s),5.07 (2 H, s), 6.78 (2 H, s), 7.0–7.5 (8 H,m) and 7.53 (1 H, s)

EXAMPLE 10
Methyl 2-[2-((((1-methyl-3-(4'-chlorophenyl)-2-propenylidene)amino) oxy)methyl)phenyl]-2-methoxyiminoacetate (Compound 1.42, Table 1).

In a 250 ml single neck flask was charged a suspension of 60% sodium hydride 0.2 g (5.0 mmoles, 1.03 eq., washed with n-hexane) in 10 ml of N,N-dimethylformamide (DMF). To this agitated suspension, stirring at room temperature, was added dropwise 0.95 g of 4-(4-chlorophenyl)-3-buten-2-one 2-oxime (4.87 mmoles, 1.0 eq) in 10 ml of N,N-dimethylformamide After 30 minutes, 1.44 g (5.01 mmoles, 1.01 eq) of methyl 2-(2-methylphenyl)-2-methoxyiminoacetate in 10 ml of DMF was added to the reaction mixture and they were agitated continuously for 2 hours at room temperature. The reaction mixture was poured into 50 ml of water, extracted with 2×50 ml of ethyl acetate. The combined organic extracts were washed with 3×50 ml of water, dried and concentrated, to obtain the crude product. This was subjected to silica gel column chromatography, using a 1:2 mixture of ethyl acetate and petroleum ether as the eluting solution to obtain 0.57 g of methyl 2-[2-((((1-methyl-3-(4'-chlorophenyl)-2-propenylidene)amino)oxy)-methyl)phenyl]-2-methoxyiminoacetate (single oxime isomer) as a faint yellow oily substance in 29.2% yield.
$^1$HNMR (90 MHz, CDCl3): 2.12 (3 H, s), 3.83 (3 H, s), 4.03 (3 H,s), 5.08 (2 H, s), 6.82 (2 H, d) and 7.1–7.5 (8 H, m).

EXAMPLE 11
N-Methyl 2-[2-((((1-methyl-3-(4'-chlorophenyl)-2-propenylidene)amino)oxy) methyl)phenyl]-2-methoxyiminoacetamide (Compound 2.03, Table 1).

In a 100 ml round bottom flask was added 0.25 g (0.625 mmoles, 1.0 eq) of methyl 2-[2-((((1-methyl-3-(4'-chlorophenyl)-2-propenylidene)amino)oxy)-methyl) phenyl]-2-methoxyiminoacetate (compound 1.42) and 0.097 g of 40% aqueous methylamine (1.250 mmols, 2.0 eq) were agitated overnight in methanol 30 ml. After concentrating the mixture, it was extracted with 2×50 ml ethyl acetate. The pooled extract was washed three times with water, and then dried and concentrated, to obtain a crude product. It was subjected to column chromatography using a 1:2 mixture of ethyl acetate and petroleum ether as the eluting solution, to obtain 0.21 g of the title compound as a faintly yellow oily substance in 84% yield.

$^1$HNMR (90 MHz, CDCl3): 2.11 (3 H, s), 2.90 (3 H, d), 3.96 (3 H, s), 5.10 (2 H, s), 6.57(1 H, br), 6.81 (2 H, s) and 7.1–7.7 (8 H, m).

EXAMPLE 12

Proton NMR data (200 MHz) are provided in Table III for typical representative compounds of Tables I and II.

TABLE III

| Compd # | Proton NMR δ (chemical shifts rel. to TMS) |
|---|---|
| 1.16 | 2..02(s, 3H), 3.68(s, 3H), 3.77(s, 3H), 5.12(s, 2H), 6.8–7.2(ABq, 2H), and 7.0–7.8(m, 9H). |
| 1.17 | 2.07(s, 3H), 3.68(s, 3H), 3.79(s, 3H), 5.11(s, 2H), 6..79–6.80(ABq, 2H), and 6.9–7.7(m, 9H). |
| 1.22 | 2.10(s, 3H), 3.69(s, 3H), 3.81(s, 3H), 5.11(s, 2H), 6..80–7.11(ABq, 2H), and 7.2–7.7(m, 8H). |
| 1.28 | 2.02(s, 3H), 3.68(s, 3H), 3.77(s, 3H), 5.12(s, 2H), 6..8–7.2(ABq, 2H), and 7.0–7.8(m, 9H). |
| 1.32 | 0.79–0.87 (m, 4H), 1.7–1.8(m, 1H), 3.61(s, 3H), 3.79(s, 3H), 5.04(s, 2H), and 7.1–7.8(m, 11H). |
| 1.36a | 3.61(s, 3H), 3.74(s, 3H), 5.20(s, 2H), 6.60–6.65(d, 1H), and 7.2–7.5(m, 14H). |
| 1.36b | 3.65(s, 3H), 3.74(s, 3H), 5.09(s, 2H), 6.3–6.4 6.8–6.9(ABq, 2H), and 7.1–7.8(m, 14H). |
| 1.54a | 2.04(s, 3H), 3.84(s, 3H), 4.04(s, 3H), 5.07(s, 2H), 6..72–6.85 (ABq, 2H), and 7.0–7.5(m, 8H). |
| 1.54b | 2.06(s, 3H), 3.72(s, 3H), 4.02(s, 3H), 5.04(s, 2H), and 6..80–7.6(m, 10H). |

Note: $^1$HNMR spectrum was recorded, using CDCl$_3$. Following codes were used: s = singlet, d = doublets, t = triplets, m = multiplets, br = broad peak

EXAMPLE 13

Numerous compounds of this invention were tested for fungicidal activity in vivo against the diseases described below. The compounds were dissolved in a 1:1 mixture of acetone and methanol 2:1:1 or N,N-dimethylformamide and diluted with a 2:1:1 mixture of water, acetone and methanol (by volume) to achieve the appropriate concentration. The solution was sprayed onto the plants and allowed to dry for two hours. Then the plants were inoculated with fungal spores. Each test utilized control plants which were sprayed with the appropriate solvent and inoculated. For these protective tests, the plants were inoculated one day after treating the plants with the compounds of this invention. The remainder of the technique of each of the tests is given below along with the results for various compounds described herein by the Compound # against the various fungi at a dose of 100 or 150 grams per hectare. The results are percent disease control as compared to the untreated check wherein one hundred was rated as complete disease control and zero as no disease control. The percent disease control is reported in activity groups wherein A is 90–100% disease control, B is 70–89% control, C is 50–69% control and D is less than 50% disease control. The application of the test fungal spores to the test plants was as follows:

Wheat Leaf Rust (WLR)

Puccinia recondita (f. sp. tritici) was cultured on 7-day old wheat (cultivar Fielder) over a 12-day period in the greenhouse. Spores were collected from the leaves by settling on aluminum foil. The spores were cleaned by sieving through a 250-micron opening screen and stored dry. The dried spored were used within one month. A spore suspension was prepared from dry uredia by adding 20 mg (9.5 million spores) per ml of Soltrol® oil. The suspension was dispensed into gelatin capsules (0.7 ml capacity) which attach to the oil atomizers. One capsule is used per flat of twenty 2-inch square pots of 7-day old plants, cultivar Fielder. After waiting for at least 15 minutes for the oil to evaporate from the wheat leaves, the plants were placed in a dark mist chamber (18–20° C. and 100% relative humidity) for 24 hours. The plants were then placed in the greenhouse and evaluated after 12 days for disease.

Wheat Leaf Blotch (SNW)

Cultures of Septoria nodorum was maintained on Czapek-Dox V-8 juice agar plates in an incubator at 20° C. with alternating periods of 12 hours of light and 12 hours of darkness for 2 weeks. A water suspension of the spores was obtained by shaking the portion of the plate with fungal material in deionized water and filtering through cheesecloth. The spore-containing water suspension was diluted to a spore concentration of 3.0×106 spores per ml. The inoculum was dispersed by a DeVilbiss atomizer over one-week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

Erysiphe graminis (f. sp. tritici) was cultured on wheat seedlings, cultivar Fielder, in a controlled temperature room at 18° C. Mildew spores were shaken from the culture plants onto 7-day old wheat seedlings which had been previously sprayed with the fungicide compound. The inoculated seedlings were kept in a controlled temperature room at 18° C. and subirrigated. The percent disease control was rated 7 days after the inoculation.

Cucumber Powdery Mildew (CPM)

Sphaerotheca fuilginea was maintained on cucumber plants, cultivar Bush Champion, in the greenhouse. Inoculum was prepared by placing five to ten heavily mildewed leaves in a glass jar with 500 ml of water containing 1 drop of Tween® 80 per 100 ml. After shaking the liquid and leaves, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Tomato Late Blight (TLB)

Cultures of Phytophthora infestans were maintained on green pea-amended agar for two to three weeks. The spores were washed from the agar with water and dipsersed with a DeVilbiss atomizer over the leaves of 3-week old Pixie tomato plants which had been previously treated with compound of the present invention. The inoculated plants were placed in a humidity cabinet at 20° C. for 24 hours for infection. The plants were then removed to a controlled environment room at 20° C. and 90% humidity. The plants were scored for disease control after five days.

Grape Downy Mildew (GDM)

Plasmopara viticola was maintained. leaves of grape plants, cultivar Delaware, in a controlled temperature chamber at 20° C. in humid air with moderate light intensity for 7 to 8 days. A water suspension of the spores from infested leaves was obtained and the spore concentration was adjusted to about 3×10$^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

Rice Blast (RB)

Cultures of *Pyricularia oyrzae* were maintained on potato dextrose agar for two to three week. The spores were washed from the agar with water containing 1 drop of Tween 80 per 100 After filtering the spore suspension through two layers of cheese cloth, the spore count was adjusted to $5\times10^5$. The spore suspension was sprayed onto 12-day old rice plants, cultivar M-1, using a DeVilbiss atomizer. The inoculated plants were placed in a humidity at chamber 20° C. for 36 hours to allow for infection. After the infection period the plants were placed in the greenhouse. After 6 days, the plants were scored for disease control.

Botrytis on Cucumber (BOT)

Cucumber plants were maintained in the greenhouse. Large, fully expanded leaves were collected from the plates. The stems were wrapped with cotton, the leaves were placed in a large petri plate (15-cm. diameter) and the leaves were supported by glass rods. The upper cover of the plate was removed and the upper surface of the detached cucumber leaf was sprayed with the compounds of the present invention. The leaf was allowed to dry in the air for approximately 2 hours. The cultures of *Botrytis cinerea* were maintained on potato dextrose agar for two to three weeks. Agar plugs, 6-mm. in diameter, were cut with a cork borer from the periphery of the fungal colony margin, These agar plugs were placed with the fungal surface in contact with the treated upper surface of the cucumber leaf. Each leaf received two mycelial plugs. After placing the petri plate cover over the leaves, the plates were returned to a controlled environmental chamber at 20° C. and 90% humidity for three to four days. After this time, the diameter of the lesions produced by the mycelial plug was measured. The average lesion size was compared to the lesion size produced on the control leaves. Data were expressed as percent control.

Cucumber Downy Mildew (CDM)

Cucumber plants were maintained in the greenhouse. Large, fully expanded leaves were collected from the plates. The stems were wrapped with cotton, the leaves were placed in a large petri plate (15-cm. diameter) and the leaves were supported by glass rods. The upper cover of the plate was removed and the upper surface of the detached cucumber leaf was sprayed with the compounds of the present invention. The leaf was allowed to dry in the air for approximately 2 hours. The cultures of *Pseudoperonospora cubensis* were maintained on cucumber plants. After extracting the spores by shaking the leaves in water, the lower surface of the treated cucumber leaves were sprayed with a spore concentration of 100,000 spores per ml. The plates were returned to a controlled environmental chamber at 20° C. and 90% humidity for five days. After this time, leaves were examined for disease development. Data were expressed as percent control.

Rhizoctonia Sheath Blight (RSB)

Broad bean plants were maintained in the greenhouse. Fully-expanded leaves, contaning two leaflets, were collected from the plates. The stems were wrapped with cotton, the leaves were placed in a large petri plate (15-cm. diameter) and the leaves were supported by glass rods. The upper cover of the plate was removed and the upper surface of the detached broad bean leaf was sprayed with the compounds of the present invention. The leaf was allowed to dry in the air for approximately 2 hours. The cultures of *Rhizoctonia solani* were maintained on potato dextrose agar for one week. Agar plugs, 6-mm. in diameter, were cut with a cork borer from the periphery of the fungal colony margin, These agar plugs were placed with the fungal surface in contact with the treated upper surface of the broad bean leaf. Each leaf received two mycelial plugs. After placing the petri plate cover over the leaves, the plates were returned to a controlled environmental chamber at 20° C. and 90% humidity for five days. After this time, the diameter of the lesions produced by the mycelial plug was measured. The average lesion size was compared to the lesion size produced on the control leaves. Data were expressed as percent control.

When tested against wheat leaf rust at 150 grams per hectare compounds 1.03a, 1.03b, 1.05, 1.07, 1.10, 1.12, 1.14, 1.16, 1.17, 1.18, 1.26, 1.42 and 2.03 exhibited control in the A rating group.

When tested against wheat leaf blotch at 150 grams per hectare compounds 1.03a, 1.03b, 1.10, 1.16, 1.17, 1.18 and 2.03 exhibited control in the A rating group.

When tested against wheat powdery mildew at 150 grams per hectare compounds 1.03a, 1.05, 1.07, 1.13, 1.16, 1.18 and 1.32 exhibited control in the A rating group.

When tested against cucumber powdery mildew at a dose of 150 grams per hectare, compounds 1.03a, 1.03b, 1.05, 1.10, 1.12, 1.16, 1.17, 1.18 and 2.03 exhibited control in the A rating group ($\geq$90% control).

When tested against tomato late blight at 150 grams per hectare compounds 1.03a, 1.03b, 1.12, 1.16, 1.17, 1.14, 1.18, 1.42 and 2.03 exhibited control in the A rating group.

When tested against grape downy mildew at 150 gram per hectare compounds 1.03a, 1.03b, 1.05, 1.07, 1.10, 1.12, 1.14, 1.16, 1.17, 1.18, 1.26, 1.28, 1.32, 1.42 and 2.03 exhibited control in the A rating group.

When tested against rice blast at 150 grams per hectare compounds 1.03a, 1.03b, 1.10, 1.10, 1.16, 1.17 and1.18 exhibited control in the A rating group.

When tested against cucumber grey mold at 100 grams per hectare compounds 1.03a, 1.03b, and 1.42 exhibited control in the A rating group. When tested at 100 grams per hectare.

Compounds 1.05, 1.10, 1.14, 1.18 and 2.03 exhibited control in the B rating group.

When tested against cucumber downy mildew at 100 grams per hectare compounds 1.01, 1.03a, 1.03b, 1.05, 1.07, 1.10, 1.12, 1.13, 1.14, 1.18, 1.42 and 2.03 exhibited control in the A rating group.

When tested against rhizoctonia sheath blight at 100 grams per hectare compounds 1.05 and 1.14 exhibited control in the A rating group Compounds 1.01, 1.03a, 1.10, 1.12, 1.13, 1.42 and 2.03 exhibited control in the B rating group.

The compounds of this invention are useful as agricultural fungicides and, as such, can be applied to various loci such as the seed, the soil or the foliage of plants to be protected.

The compounds of this invention can be applied as fungicidal sprays by methods commonly employed, such as conventional high-volume hydraulic sprays, low-volume sprays, air-blast\spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fingicide the chemical can be incorporated in the soil or applied to the surface usually at a rate of from about 0.02 to about 20, preferably from about 0.05 to about 10, and more preferably from about 0.1 to about 5 kilograms per hectare. As a foliar fingicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15). Other known fungicides which an be combined with the compounds of this invention are dimethomorph, cymoxanil, thifluzamide, furalaxyl, ofurace, benalaxyl, oxadixyl, propamocarb, cyprofuram, fenpiclonil, fludioxonil, pyrimetbanil, cyprodinil, triticonazole, fluquinconazole, metconazole, spiroxamine, carpropamid, azoxystrobin, kresoxim-methyl, metominostrobin and trifloxystrobin.

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, barley stripe and leaf rust, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast

EXAMPLE 14

Numerous compounds of this invention were tested for insecticidal activity in vivo against the insects described below. The following test method was used to evaluate compounds of the present invention for insecticidal activity. The compound to be evaluated was dissolved in an appropriate solvent, usually a mix of acetone, methanol and water, and sprayed over three excised leaf disks using a flat fan nozzle. After spraying, the leaf disks were allowed to dry. Two disks were infested with the leaf chewing insects (southern armyworm and Mexican bean beetle) and the third leaf disk was already infested with the two-spotted spider mite prior to spraying. The tested insect species were:

| | | |
|---|---|---|
| AW | southern armyworm | *Spodoptera eridamia* |
| BB | Mexican bean beetle | *Epilachna varivestis* |
| MTA | two-spotted spider mite | *Teranychus uricate* |

Observations as percent control were made by visual inspection 24–48 hours after spraying.

When tested against southern army worm at 300 grams per hectare compounds 1.03a, 1.05, and 1.13 provided 50% or better control and when tested at 150 grams per hectare compounds 1.16, 1.17, 1.18, 1.32 and 2.03 provided 50% or better control.

When tested against Mexican bean beetle at 300 grams/hectare compounds 1.03a, 1.05, 1.07, 1.13, provided 50% or better control and when tested at 150 grams per hectare 1.16, 1.18, 1.22 and 1.32 provided 50 % or better control.

When tested against two-spotted spider mite at 300 grams/hectare compound 1.05 provided 50% or better control and when tested at 150 grams per hectare compound 1.16, provided 50% or better control.

EXAMPLE 15

Anti-feeding activity and lethal activity were tested with armyworms (Leucaniar Separata). A certain number of trimester larva were released in a culture dish, and they were cultivated with the drug-treated corn steep liquor. Potter spraying tower was employed as the method of drug administration. Amount sprayed was 1 ml, spray pressure was 13.5 lb/in$^2$ (93 kPa), and concentrations of the applied compound was 500 ppm and 120 ppm. Test results are presented in the following table. The percentage of food consumed, as shown in the table, should relate to the number of organisms remaining and their health.

TABLE IV

| | | 24 hrs | | 48 hrs | | 5 days | |
|---|---|---|---|---|---|---|---|
| Compound # | Dose (ppm) | Death (%) | % Food Consumed | Death (%) | % Food Consumed | Death (%) | % Food Consumed |
| 1.03a | 500 | 0 | 3 | 40 | 5 | 80 | 10 |
| 1.03a | 120 | 0 | 15 | 0 | 25 | 0 | 40 |
| 1.05 | 500 | 0 | 0 | 60 | 3 | 100 | 3 |
| 1.05 | 120 | 0 | 10 | 0 | 15 | 20 | 20 |
| Blank | | 0 | 100 | 0 | 100 | 0 | 100 |

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as systemic application. Alternatively, the active compound may be applied to the soil and contacted therein with the insects and other pests to be controlled. This means of application is referred to as soil application. In another alternative, the active compound may be foliarly applied to the plants to be freed from insects and other pests which feed on the foliage.

Compositions and formulations according to the present invention may also include known pesticidal compounds. This expands the spectrum of activity of the preparation and may give rise to synergism. Suitable insecticides known in the art include those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. A listing of such adjuvants commonly used in the art, and a discussion of adjuvants, can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001 (1:999,999) –99 (99:1) % by weight. For compositions suitable for storage or transportation, the amount of active ingredient is preferably between about 0.5 (1:199) –90 (9:1) % by weight, and more preferably between about 1 (1:99) –75 (3:1) % by weight of the mixture. Compositions suitable for direct application or field application generally contain the active compound in an amount substantially between about 0.0001 (1:999,999) –95 (19:1) %, preferably between about 0.0005 (1:199,999) –90 (9:1) % by weight, and more preferably between about 0.001 (1:99,999) –75 (3:1) % by weight of the mixture. The composition can also be stated as a ratio of the compound to the carrier. In the present invention the weight ratio of these materials (active compound/carrier) can vary from 99:1 (99%) to 1:4 (20%) and more preferably from 10:1 (91%) to 1:3 (25%).

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clay, inorganic silicate and carbonate, and silica and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide, such as that sold under the trademark Hi-Sil®, and 5 parts of sodium lignosulfonate. In another preparation a kaolin type (Barden) clay is used in place of the Hi-Sil® in the above wettable powder, and in another such preparation 25% of the Hi-Sil® is replaced with a synthetic sodium silicoaluminate sold under the trademark Zeolex®3.

Dusts are prepared by mixing compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which comprises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. A compound of the formula:

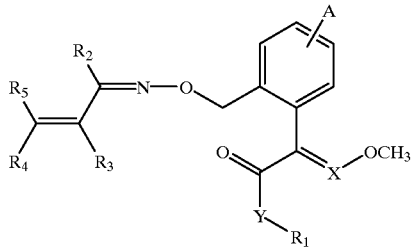

wherein X is N or CH; Y is O, S, or $NR_6$;

A is hydrogen, halo, cyano, $(C_1-C_{12})$alkyl, or $(C_1-C_{12})$alkoxy;

$R_1$ and $R_6$ are independently hydrogen or $(C_1-C_4)$alkyl;

$R_2$ is hydrogen, $(C_1-C_{12})$alkyl, halo$(C_1-C_{12})$alkyl, $(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl;

$R_8$ is hydrogen or $(C_1-C_4)$alkyl;

$R_4$ and $R_5$ are independently hydrogen, $(C_1-C_4)$alkyl, substituted aryl, aralkyl, aryl$(C_2-C_8)$alkenyl, aryl $(C_2-C_8)$alkynyl, wherein no more than one of $R_4$ and $R_5$ is selected from the group of hydrogen and $(C_1-C_4)$alkyl;

and enantiomers, stereoisomers, and agronomically acceptable salts thereof.

2. The compound of claim 1 wherein X is CH, Y is O, $R_2$ is $(C_1-C_{12})$alkyl, and $R_3$ is hydrogen.

3. The compound of claim 2 wherein one of $R_4$ and $R_5$ is selected from the group consisting of 2-chlorophenyl, 2-fluorophenyl, 2-trifuoromethylphenyl, 3-chlorophenyl, 8-fluorophenyl, 3-trifluoromethylphenyl, 4-chlorophenyl, 4-fluorophenyl, 4-trifluoromethylphenyl and 2,4-dichlorophenyl.

4. The compound of claim 1 wherein X is N, Y is O or NH, $R_2$ is $(C_1-C_{12})$alkyl and $R_3$ is hydrogen.

5. The compound of claim 4 wherein one of $R_4$ and $R_5$ is independently selected from the group consisting of 2-chlorophenyl, 2-fluorophenyl, 2-trifluoromethylphenyl, 3-chlorophenyl, 3-fluorophenyl, 3-trifluoromethylphenyl, 4-chlorophenyl, 4-fluorophenyl, 4-trifluoromethylphenyl and 2,4-dichlorophenyl.

6. The compound of claim 1 where the compound is methyl 3-methoxy-2-[2-((((1-methyl-3-(2'-chlorophenyl)-2-propenylidene)amino)oxy)methyl)phenyl]propenoate.

7. The compound of claim 1 where the compound is methyl 3-methoxy-2-[2-((((1-methyl-3-(4'-chlorophenyl)-2-propenylidene)amino)oxy)methyl)phenyl]propenoate.

8. A fungicidal composition for controlling phytopathogenic fungi which comprises an agronomically acceptable carrier and the compound of claim 1 wherein the ratio of the carrier to the compound is between 99:1 and 1:4.

9. A method for controlling phytopathogenic fungi which comprises applying the compound of claim 1 to the locus where control is desired, at a rate of from 0.005 to 50 kilograms per hectare.

10. A method for controlling insects which comprises applying to the insect's habitat the compound of claim 1 at a rate of from 0.0005 to 10 kilograms per hectare.

* * * * *